US00PP30130P2

(12) United States Plant Patent
Korlipara

(10) Patent No.: US PP30,130 P2
(45) Date of Patent: Jan. 22, 2019

(54) ***LEUCANTHEMUM* PLANT NAMED 'ADORABLE'**

(50) Latin Name: ***Leucanthemum* x *superbum***
Varietal Denomination: Adorable

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/732,369

(22) Filed: Oct. 31, 2017

(51) Int. Cl.
*A01H 5/02* (2018.01)

(52) U.S. Cl.
USPC ..... Plt./285

(58) Field of Classification Search
USPC ..... Plt./263.1, 284, 285
See application file for complete search history.

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A new and distinct *Leucanthemum* plant named 'Adorable' characterized by small, double, daisy-type inflorescences, light yellow ray florets in bud, an excellent crown count, a small, compact, upright habit, and excellent vigor.

1 Drawing Sheet

Botanical denomination: *Leucanthemum* x *superbum.*
Variety designation: 'Adorable'.

BACKGROUND OF THE INVENTION

The present invention relates to a new and distinct cultivar of *Leucanthemum* and given the cultivar name 'Adorable'. *Leucanthemum* is in the family Asteraceae. This new cultivar originated from a controlled cross between unknown, unnamed, proprietary *Leucanthemum* x *superbum* seedlings. This was part of a controlled breeding program to obtain dwarf *Leucanthemum. Leucanthemum* 'Adorable' was selected for its white double daisy inflorescences and its upright, compact, small habit.

Compared to *Leucanthemum* x *superbum* 'Bridal Bouquet', U.S. Plant Pat. No. 24,260, the new cultivar has a more upright habit and smaller, more numerous inflorescences.

This new *Leucanthemum* cultivar is distinguished as unique with its:

1. small, double, daisy-type inflorescences,
2. light yellow ray florets in bud,
3. an excellent crown count,
4. a small, compact, upright habit, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a single, 1 year old plant of the new cultivar growing in full sun in the trial field in early July in Canby, Oreg.

FIG. 2 shows an expanded view of 4 plants of the new cultivar in the field plant out in full sun in early July of Canby, Oreg.

DETAILED PLANT DESCRIPTION

The following is a detailed description of the new *Leucanthemum* cultivar based on observations of 2-year-old specimens growing in the garden in sun under typical outdoor conditions in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart, 5th* edition, 2007.

Plant:
- *Type.*—Herbaceous perennial.
- *Hardiness.*—USDA Zones 5 to 9.
- *Size.*—44 cm wide and 36 cm tall to top of inflorescences.
- *Form.*—Basal clump.
- *Number of crowns.*—38.
- *Vigor.*—Excellent.

Stem (flowering):
- *Type.*—Ascending.
- *Size.*—Grows to about 25 to 30 cm tall to a terminal inflorescence and 8 mm wide at base.
- *Number of stems.*—About 38 stems from the crown, each flowering with 1 to 10 inflorescences.
- *Internode length.*—1 to 1.5 cm.
- *Strength.*—Excellent, very strongly upright.
- *Surface texture.*—Pubescent.
- *Color.*—Yellow Green 146B.

Leaf:
- *Type.*—Simple.
- *Shape.*—Lanceolate.
- *Arrangement.*—Alternate.
- *Blade size.*—Grows to 8.5 cm long and 21 mm wide.

*Margins*.—Serrate.

*Apex*.—Obtuse.

*Base*.—Clasping.

*Petiole*.—Sessile.

*Surface texture*.—pubescent on both sides.

*Venation*.—Pinnate, main vein top side Yellow Green 147C, bottom side Yellow Green 148D.

*Color*.—Topside Green N137D, bottom side Yellow Green 147B.

Inflorescence:

*Type*.—Composite on terminal stalked heads.

*Number of inflorescences per plant*.—About 90.

*Size*.—5 to 6 cm wide and 2 cm deep.

*Form*.—Ray florets are held horizontally, mature disc is rounded.

*Immature inflorescence* (*from a terminal bud*).—15 mm wide and 12 mm deep, ray florets held vertically and cupped slightly inwards, Yellow 4C.

*Ray florets*.—With 1 pistil and no stamen, about 100 in number, 70 normal size and 30 of reduced size, normal ray florets oblong, tip with 3 small lobes, margins entire, base attenuate, grows to 24 mm long and 9 mm wide, reduced ray florets linear to 2-laciniate segments cut to the base, usually 24 mm long and 3.5 mm wide, tip acute, margins entire, base attenuate, both sizes glabrous and White NN155D on both sides; pistil 5 mm long, ovary 1.5 mm long, Yellow Green 149D, style 2.5 mm long, White 155A, 2-branched stigma 0.5 mm long, Yellow 13B.

*Disc*.—Slightly concave becoming convex, becoming 12 mm deep and 20 mm wide with maturity, Yellow Orange 16A.

*Disc florets*.—About 420 in number, each 6 mm long and 1.5 mm wide; corolla tubular, 4.5 mm long and 1.5 mm wide, 5 lobed, inside and out glabrous and Yellow 12A on top ½ and Yellow Green 145C on bottom ½; pistil 1, 5.5 mm long, ovary 2.5 mm long and Yellow Green 145D, style 2 mm long, Greyed Orange 163B, 2 branched stigma 1 mm long, Greyed Orange 163B; stamen 5 in number, 4 mm long, filaments 2 mm long, Greyed Orange 163B, anthers 2 mm, Greyed Orange N163B, pollen Yellow Orange N25A.

*Involucral bracts*.—In 3 imbricate whorls, area 1.8 to 2.8 cm wide and 8 mm deep, lobes lanceolate in shape, grow to 7 mm long and 3 mm wide, Green 138B with margin membranous and Brown 200B, tip acute to piliferous, pubescent on back side and glabrous on inside.

*Receptacle*.—Grows to 10 mm wide and 5 mm deep, Yellow Green 145D.

*Bloom period*.—July through August in Canby, Oreg.

*Fragrance*.—None.

*Lastingness*.—Each inflorescence lasts about two weeks in Canby, Oreg.

Seeds: Few, each 3 mm long and 2 mm wide, oval, Brown 200C.

*Fertility*.—Poor.

Disease and pests: No problems have been found in Canby, Oreg. in the last 4 years. No known resistances to pests or diseases.

I claim:

1. A new and distinct *Leucanthemum* plant as herein illustrated and described.

* * * * *

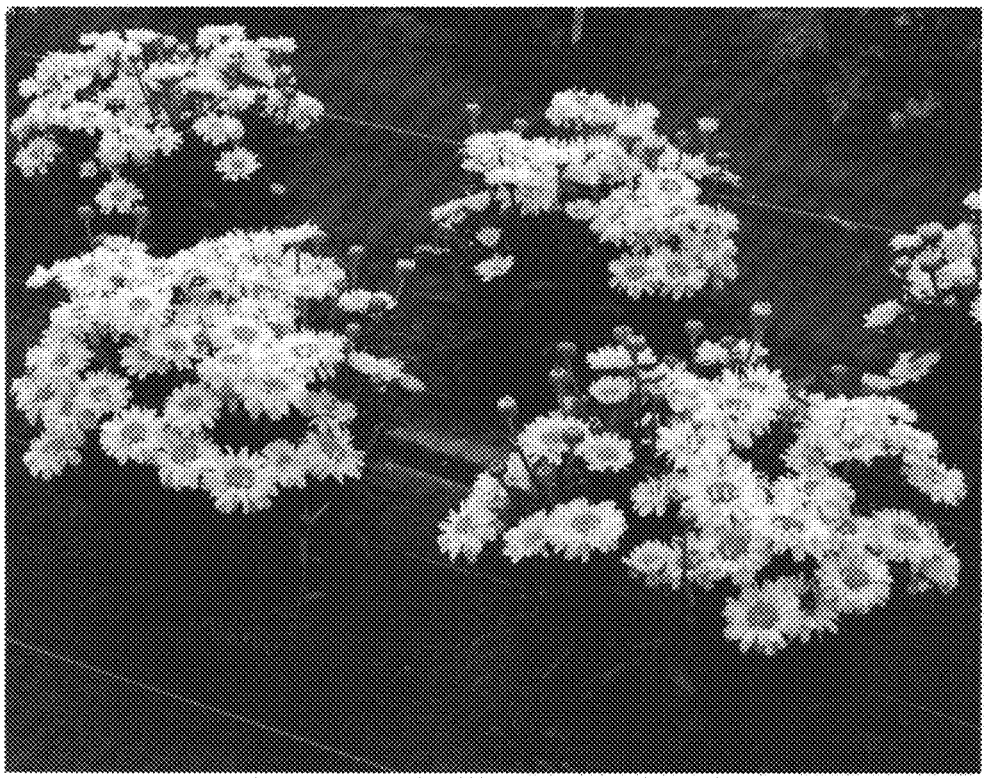

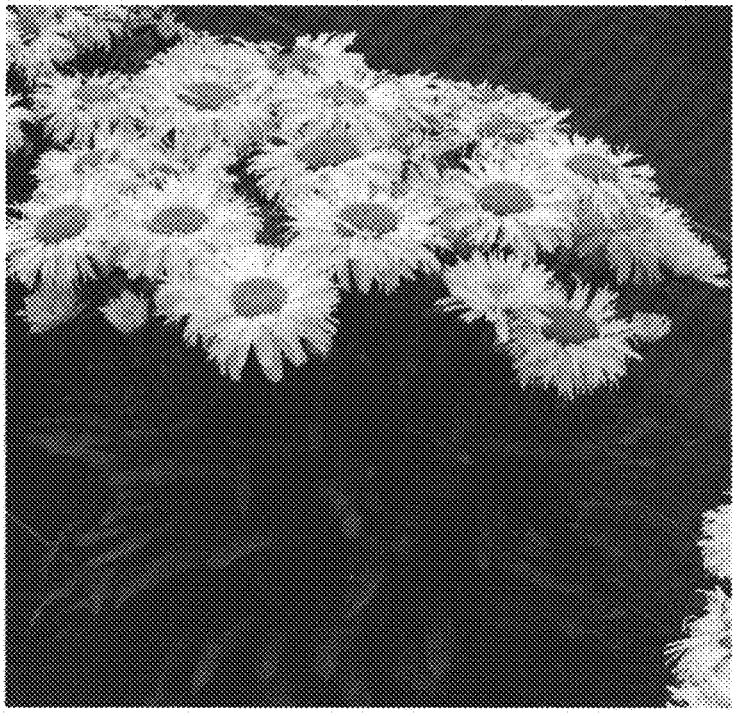
FIG. 1 on left
FIG. 2 below